(12) United States Patent
Bruls et al.

(10) Patent No.: US 8,228,506 B2
(45) Date of Patent: Jul. 24, 2012

(54) MICROELECTRONIC SENSOR DEVICE WITH A MODULATED LIGHT SOURCE

(75) Inventors: Dominique Maria Bruls, Eindhoven (NL); Johannes Joseph Hubertina Barbara Schleipen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 253 days.

(21) Appl. No.: 12/670,148

(22) PCT Filed: Jul. 17, 2008

(86) PCT No.: PCT/IB2008/052869
§ 371 (c)(1),
(2), (4) Date: Jan. 22, 2010

(87) PCT Pub. No.: WO2009/016533
PCT Pub. Date: Feb. 5, 2009

(65) Prior Publication Data
US 2010/0165345 A1    Jul. 1, 2010

(30) Foreign Application Priority Data

Jul. 31, 2007  (EP) .................................. 07113478

(51) Int. Cl.
*G01B 9/02* (2006.01)
*G01N 21/00* (2006.01)
*G01N 21/55* (2006.01)
(52) U.S. Cl. .................. 356/450; 356/432; 356/445
(58) Field of Classification Search ............ 356/432, 356/436, 441, 442, 450, 445
See application file for complete search history.

(56) References Cited

U.S. PATENT DOCUMENTS

| 4,764,934 A * | 8/1988 | Kwong et al. ............. 372/46.01 |
| 5,313,448 A | 5/1994 | Sukeda |
| 5,909,278 A | 6/1999 | Deka |
| 6,816,256 B1 | 11/2004 | Lloyd |
| 6,881,589 B1 * | 4/2005 | Leland et al. .............. 436/164 |
| 2005/0048599 A1 | 3/2005 | Goldberg |
| 2005/0239210 A1 * | 10/2005 | Iida ............................ 436/164 |

OTHER PUBLICATIONS

Stubkjaer, K. et al "Noise Properties of Semiconductor Lasers due to Optical Feedback" IEEE Journal of Quantum Electronics, vol. QE-20, No. 5, May 1984, pp. 472-478.
Stubkjaer, K. et al "Feedback-Induced Noise in Index-Guided Semiconductor Lasers and its Reduction by Modulation" Electronics Letters, vol. 19, No. 10, May 1983, pp. 388-390.
Small M.B. et al "Noise Porperties of Semiconductor Lasers in Simulated Conditions of Optical Playback" Topical Meeting on Optical Data Sorage, Apr. 1984.

* cited by examiner

Primary Examiner — Michael A Lyons

(57) ABSTRACT

A microelectronic sensor device and a method for making optical examinations at a carrier for the detection of magnetic particles, for example, at a contact surface of the carrier by frustrated total internal reflection (FTIR), include a light source with a laser modulator for emitting an input light beam into the carrier. The input light beam is modulated such that optical interferences with reflections of the input light beam from the entrance window, or from other components of the carrier, are reduced or minimized. This can be achieved by a pulsed on/off modulation in which the first relaxation minimum of a currently emitted pulse ($P_N$) coincides in the light source with the first relaxation maximum of a reflected pulse ($P_{N-1}'$). By reducing the effect of interferences, the setup is less prone to disturbances from dimensional variations that are induced by thermal extension, for example.

16 Claims, 2 Drawing Sheets

… … …

MICROELECTRONIC SENSOR DEVICE WITH A MODULATED LIGHT SOURCE

The invention relates to a microelectronic sensor device and a method for optical examinations at a carrier with the help of a light source. Moreover, it relates to the use of such a device.

The US 2005/0048599 A1 discloses a method for the investigation of microorganisms that are tagged with particles such that a (e.g. magnetic) force can be exerted on them. In one embodiment of this method, a laser beam is directed through a transparent material to a surface where it is totally internally reflected. Light of this beam that leaves the transparent material as an evanescent wave is scattered by microorganisms and/or other components at the surface and then detected by a photodetector or used to illuminate the microorganisms for visual observation. A problem of this and similar setups is that interferences of the emitted laser light with reflections of this light may occur that change over time and thus cause undesired variations of the laser light output.

Based on this situation it was an object of the present invention to provide alternative means for making optical examinations with the help of a light source, wherein it is desired that the examinations are more robust with respect to variations in the light output.

The microelectronic sensor device according to the present invention serves for optical examinations at a carrier, wherein the carrier does not necessarily belong to the device. The carrier will usually be made from a transparent material, for example glass or polystyrene, to allow the propagation of light of a given spectrum. Its concrete design depends on the application it is intended for. Moreover, it should be noted that the term "examination" is to be understood in a broad sense, comprising any kind of manipulation and/or interaction of light with some entity in or at the carrier. The examinations may preferably comprise the qualitative or quantitative detection of target components comprising label particles, wherein the target components may for example be biological substances like biomolecules, complexes, cell fractions or cells.

The microelectronic sensor device comprises the following components:

a) A light source for emitting a light beam, called "input light beam" in the following, via an entrance window into the carrier, wherein said entrance window is a particular (planar or curved) part of the surface of the carrier. The light source will usually have some more or less pronounced coherence, though it should be noted that this coherence may be very small and actually an (undesired) side effect. The light source may for example be a laser diode or an LED (light emitting diode), optionally provided with some optics for shaping and directing the input light beam, particularly means for collimating it.

b) A modulator for modulating the light source such that optical interferences of the light source with reflections of the input light beam from the entrance window of the carrier or other components in the light path (particularly components of the carrier) are reduced (preferably minimized or completely eliminated). The modulator may be realized in many different ways which are known to a person skilled in the art of e.g. laser design. It may for example comprise an electronic circuit for supplying a laser current, i.e. the electrical current used for driving the pumping of a laser that generates an overpopulation of excited states in the laser medium.

The invention further relates to a method for optical examinations at a carrier, comprising:

a) Emitting with a light source an input light beam via an entrance window into the carrier.

b) Modulating the light source with a modulator such that optical interferences of the (more or less coherent) light source with reflections of the input light beam from the entrance window or other components are reduced.

The described microelectronic sensor device and method have the advantage to provide an input light beam which has a smaller feedback with reflections from the entrance window or other components of e.g. the carrier. With the reduction of this feedback, also variations of the feedback are reduced which may occur for example from slight dimensional changes of the optical components under thermal expansion.

Appropriate operation parameters of the modulation may be found by trial and error, i.e. by testing different settings of the modulator and observing the resulting optical interferences. In a preferred embodiment of the invention, the modulation is a priori designed in so far as it comprises a pulsed emission of the input light beam, i.e. in that the input light beam consists of a series of pulses separated in time by pauses. The pulses may all be different from each other or, preferably, all have (approximately) the same shape.

In the aforementioned case, the emitted pulses of the light source may optionally be dimensioned such that they do not coincide in the light source with previous pulses of the light source that were reflected at the entrance window or other components of e.g. the carrier. Thus the pulses that are reflected at e.g. the entrance window will not have any possibility of interference.

While the aforementioned approach is a way to reduce interferences to the absolute minimum of zero, this result can in many cases hardly be realized due to too short distances between the light source and the reflection site of pulses in combination with the minimally possible pulse duration. In another approach to modulate the input light beam of a laser light source, the pulses are therefore designed such that a (e.g. first) relaxation minimum of a currently emitted pulse coincides in the laser light source (or, more precisely, in its internal laser cavity) with a (e.g. first) relaxation maximum of a previous pulse that was reflected at the entrance window or another component of the carrier. When the laser light source is operated in pulsed mode, the output of the laser shows intensity fluctuations at the onset of the laser pulse due to the relaxation oscillation that is well known to a person skilled in the art. If timing of the laser pulses is such that the first relaxation oscillation maximum of the externally reflected pulse number (N−1) coincides with the first relaxation minimum of the currently emitted pulse number N, then the laser is rather insensitive to this optical feedback due to a depletion of the carriers in the laser device at that time instance.

For many practical applications, it has been found to be appropriate that the mentioned pulses of the input light beam are periodically repeated with a repetition frequency that ranges between approximately 100 MHz and 1 GHz. Additionally or alternatively, it is preferred that the pulses have a duty cycle which ranges between 1% and 80% (wherein this percentage indicates the fraction of time of the period during which the pulse is "on" in contrast to the pause or "off" time). It should be noted that, if extreme short optical pulses are generated by e.g. exciting only the first relaxation oscillation of a laser, this requires an electrical addressing scheme with pulse widths in the nsec regime, regardless of modulation frequency. For a modulation with a frequency of less than 10 MHz, the 1 nsec pulse width will then imply duty cycles lower than 1%.

In the aforementioned embodiment, it was tried to prevent the pulses from interacting with each other by separating them in time domain (this has to do with laser dynamics), so to prevent RIN (laser noise) or at least to try to keep it as low as possible. In another embodiment of the invention, the laser current that drives a laser light source is modulated for introducing sidemodes into the input light beam and for making it less coherent. Thus any constructive/destructive interference effects inside the laser can be prevented that may depend on the external cavity length (which is a rather optical effect).

The described microelectronic sensor device can be applied in a variety of setups and apparatuses. In a particular example, the carrier comprises a contact surface at which the input light beam is totally internally reflected as an output light beam. To this end, the contact surface must comprise an interface between two media, e.g. glass and water, at which total internal reflection (TIR) can take place if the incident light beam hits the interface at an appropriate angle (larger than the associated critical angle of TIR). Such a setup is often used to examine small volumes of a sample at the TIR-interface which are probed by a non-propagating evanescent wave that is exponentially decaying into the medium with the lower refractive index (e.g. water). Target components—e.g. atoms, ions, (bio-)molecules, cells, viruses, or fractions of cells or viruses, tissue extract, etc. —that are present in the investigation region can then scatter or absorb the light of the evanescent waves which will accordingly miss in the reflected light beam. In this scenario of a "frustrated total internal reflection" (FTIR), the output light beam of the sensor device will consist of the reflected light of the input light beam, wherein the small amount of light missing due to scattering of evanescent waves contains the desired information about the target components at the contact surface.

In a further development of the aforementioned embodiment, a light detector is provided for determining the amount of light in the output light beam (e.g. expressed as the intensity in the cross section of the beam). The detector may comprise any suitable sensor or plurality of sensors by which light of a given spectrum can be detected, for example photodiodes, photo resistors, photocells, a CCD chip, or a photo multiplier tube.

In another embodiment of the invention, the microelectronic sensor device comprises an actuator for manipulating target particles in a sample chamber adjacent to the carrier. The target particles may particularly be magnetic particles that can be moved by a magnetic field and thus deliberately be attracted to the contact surface of the carrier and/or washed away from it. The actuator will in this case usually comprise an electromagnet or a plurality of electromagnets. The operation of such an electromagnet (or in general of an electrically driven actuator) will typically dissipate heat that induces thermal expansion of the surrounding components. This may cause uncontrollable and unpredictable variations in the interference of reflected light beams with the light source. However, as such interferences are from the beginning reduced due to the measures described above, disturbances due to said variations are much less critical.

The invention further relates to the use of the microelectronic device described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

These and other aspects of the invention will be apparent from and elucidated with reference to the embodiment(s) described hereinafter. These embodiments will be described by way of example with the help of the accompanying drawings in which.

Like reference numbers in the Figures refer to identical or similar components.

Though the present invention will in the following be described with respect to a particular setup (using magnetic particles and frustrated total internal reflection as measurement principle), it is not limited to such an approach and can favorably be used in many different applications.

Figure 1:
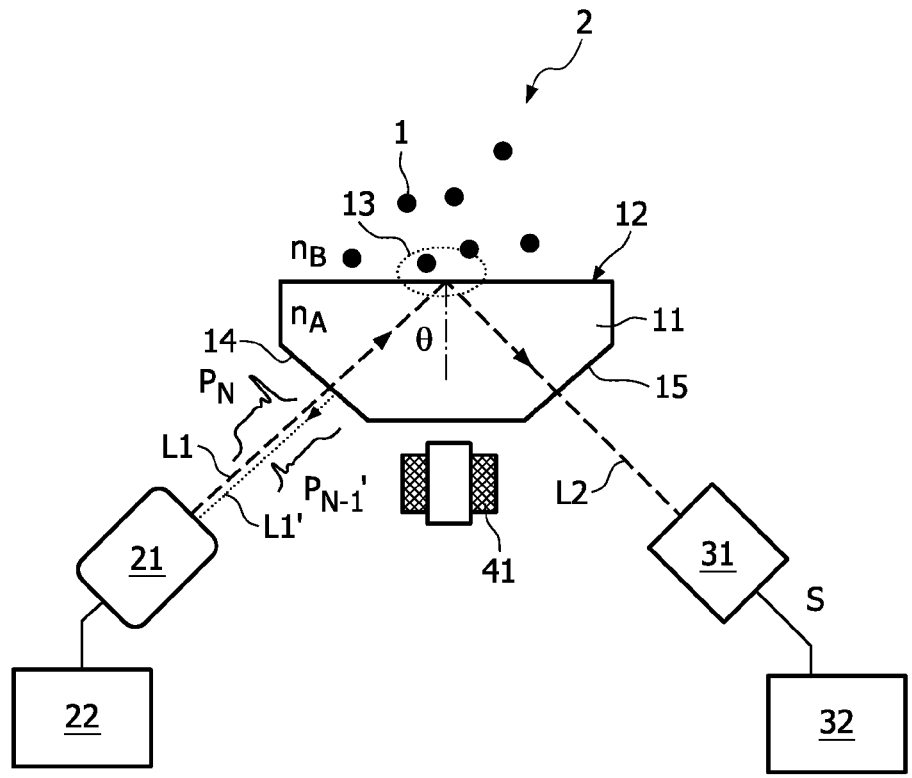
FIG. 1 shows schematically a microelectronic sensor device according to the present invention.

FIG. 1 shows a general setup with a microelectronic sensor device according to the present invention. A central component of this setup is the carrier 11 that may for example be made from glass or transparent plastic like polystyrene. The carrier 11 is located next to a sample chamber 2 in which a sample fluid with target components to be detected (e.g. drugs, antibodies, DNA, etc.) can be provided. The sample further comprises magnetic particles, for example superparamagnetic beads, wherein these particles are usually bound as labels to the aforementioned target components. For simplicity only the combination of target components and magnetic particles is shown in the Figure and will be called "target particle 1" in the following. It should be noted that instead of magnetic particles other label particles, for example electrically charged or fluorescent particles, could be used as well.

The interface between the carrier 11 and the sample chamber 2 is formed by a surface called "contact surface" 12. This contact surface 12 is coated with capture elements, e.g. antibodies, which can specifically bind the target particles.

The sensor device comprises a magnetic field generator 41, for example an electromagnet with a coil and a core, for controllably generating a magnetic field at the contact surface 12 and in the adjacent space of the sample chamber 2. With the help of this magnetic field, the target particles 1 can be manipulated, i.e. be magnetized and particularly be moved (if magnetic fields with gradients are used). Thus it is for example possible to attract target particles 1 to the contact surface 12 in order to accelerate the binding of the associated target particle to said surface. Also, an additional magnetic field generator can be incorporated at different positions, e.g. opposite to the shown magnetic field generator 41 at the other end of the contact surface 12, e.g. to wash unbound target particles away from the contact surface after an attraction phase during measurement.

The sensor device further comprises a light source 21 that generates an input light beam L1 which is transmitted into the carrier 11 through an "entrance window" 14. As light source 21, a laser like a commercial DVD ($\lambda$=658 nm) laser-diode can be used. The following description of the example will refer to such a laser light source, though e.g. an LED might be used as well. A collimator lens may be used to make the input light beam L1 parallel, and a pinhole of e.g. 0.5 mm may be used to reduce the beam diameter. The input light beam L1 arrives at the contact surface 12 at an angle larger than the critical angle $\theta_c$ of total internal reflection (TIR) and is therefore totally internally reflected in an "output light beam" L2. The output light beam L2 leaves the carrier 11 through another surface ("exit window" 15) and is detected by a light detector 31. The light detector 31 determines the amount of light of the output light beam L2 (e.g. expressed by the light intensity of this light beam in the whole spectrum or a certain part of the spectrum). The measured sensor signals S are evaluated and optionally monitored over an observation period by an evaluation and recording module 32 that is coupled to the detector 31.

It is possible to use the detector 31 also for the sampling of fluorescence light emitted by fluorescent particles 1 which were stimulated by the input light beam L1, wherein this fluorescence may for example spectrally be discriminated from reflected light L2. Though the following description concentrates on the measurement of reflected light, the principles discussed here can mutatis mutandis be applied to the detection of fluorescence, too.

The described microelectronic sensor device applies optical means for the detection of target particles 1. For eliminating or at least minimizing the influence of background (e.g. of the sample fluid, such as saliva, blood, etc.), the detection technique should be surface-specific. As indicated above, this is achieved by using the principle of frustrated total internal reflection. This principle is based on the fact that an evanescent wave decays (exponentially dropping) into the sample 2 when the incident light beam L1 is totally internally reflected. If this evanescent wave then interacts with another medium like the bound target particles 1, part of the input light will be coupled into the sample fluid (this is called "frustrated total internal reflection") or will be absorbed by the target molecules and/or label particles (e.g. magnetic beads), and the reflected intensity will be reduced (while the reflected intensity will be 100% for a clean interface and no interaction). Depending on the amount of disturbance, i.e. the amount of target particles on or very near (within about 200 nm) to the TIR surface (not in the rest of the sample chamber 2), the reflected intensity will drop accordingly. This intensity drop is a direct measure for the amount of bound target particles 1, and therefore for the concentration of target particles in the sample. When the mentioned interaction distance of the evanescent wave of about 200 nm is compared with the typical dimensions of anti-bodies, target molecules and magnetic beads, it is clear that the influence of the background will be minimal. Larger wavelengths $\lambda$ will increase the interaction distance, but the influence of the background liquid will still be very small. Also increasing of the angle of incidence $\theta$ will increase the interaction distance above the surface as well.

The described procedure is independent of applied magnetic fields. This allows real-time optical monitoring of preparation, measurement and washing steps. The monitored signals can also be used to control the measurement or the individual process steps.

For the materials of a typical application, medium A of the carrier 11 can be glass and/or some transparent plastic with a typical refractive index of 1.52. Medium B in the sample chamber 2 will be water-based and have a refractive index close to 1.3. This corresponds to a critical angle $\theta_c$ of 60°. An angle of incidence of 70° is therefore a practical choice to allow fluid media with a somewhat larger refractive index (assuming $n_A$=1.52, $n_B$ is allowed up to a maximum of 1.43). Higher values of $n_B$ would require a larger $n_A$ and/or larger angles of incidence.

Advantages of the described optical read-out combined with magnetic labels for actuation are the following:

Cheap cartridge: The carrier 11 can consist of a relatively simple, injection-molded piece of polymer material.

Large multiplexing possibilities for multi-analyte testing: The contact surface 12 in a disposable cartridge can be optically scanned over a large area. Alternatively, large-area imaging is possible allowing a large detection array. Such an array (located on an optical transparent surface) can be made by e.g. ink jet printing of different binding molecules on the optical surface. The method also enables high-throughput testing in commercially available well-plates by using multiple beams and multiple detectors and multiple actuation magnets (either mechanically moved or electro-magnetically actuated).

Actuation and sensing are orthogonal: Magnetic actuation of the target particles (by large magnetic fields and magnetic field gradients) does not influence the sensing process. The optical method therefore allows a continuous monitoring of the signal during actuation. This provides a lot of insights into the assay process and it allows easy kinetic detection methods based on signal slopes.

The system is really surface sensitive due to the exponentially decaying evanescent field.

Easy interface: No electric interconnect between cartridge and reader is necessary. An optical window is the only requirement to probe the cartridge. A contact-less read-out can therefore be performed.

Low-noise read-out is possible.

A particular advantage of the laser light source 21 that is used in the microelectronic sensor device of FIG. 1 is that a nice narrow collimated input light beam L1 can be generated to illuminate a small investigation region 13 on the contact surface 12 where the bioassay takes place. Furthermore, the laser emits light of only one wavelength, which exactly determines the angle at which total internal reflection occurs in the carrier 11. However, due to the coherence of the laser light, problems may arise as a result of optical feedback when the dimensions of the cartridge slightly change due to temperature changes. Similar problems may occur if other light sources than lasers are used, e.g. LEDs, which usually also show some (small) coherence that may provoke feedback effects. These aspects will now be discussed in more detail.

The (disposable) cartridge comprising the carrier 11 will usually consist of only simple, cheap injection molded parts, and it would be too expensive to apply antireflective coatings to the relevant surfaces of the carrier (entrance and exit window 14, 15). However, due to the absence of such a coating, some part L1' of the input light beam L1 will be reflected from the entrance window 14 back into the laser (actually, a small—unwanted—interferometer is formed in this way). This will cause laser feedback, caused by the interference of the reflected light beam L1' in the laser cavity. Normally, this will not be a problem, as the effect is constant, and the introduced noise in the laser output is averaged out easily. However, in the described FTIR biosensor, electrical components like particularly the magnetic field generator 41 are present. When the electromagnet 41 is switched on, it will dissipate heat, which will heat up the cartridge with the carrier 11 and the microelectronic sensor device itself. Now, there is a problem: due to the heating, the distance between the light source 21 and the carrier 11 can change up to several laser wavelengths ($\gg\frac{1}{10}\lambda$), thereby influencing the laser feedback and causing intensity and noise irregularities in the laser output. The heating and cooling of the cartridge-reader ensemble usually takes up to 1 minute. During this time, the laser output will fluctuate, due to the continuously changing laser feedback. Also the signal from a possible forward sense diode, which may be located in the housing of the light source 21, will be influenced. Thus a "wiggle" in the order of a few percent in the normalized optical signal can be observed, which is not caused by the bioassay (cf. curve $S_0$ in FIG. 3), but by the faulty values provided by the forward sense diode. This is highly undesirable, as this hampers proper determination of concentrations of the substances under investigation, e.g. drugs-of-abuse in saliva.

To address the aforementioned issues, it is proposed here to make the laser less sensitive to optical feedback. This can be achieved by using a so-called laser modulator 22, which supplies the laser current to the light source 21 and which is set at a proper frequency (such modulators are often used in e.g. DVD players). Modulating the laser current of the laser device causes sidemodes to appear in the optical spectrum, making the laser less coherent and consequently less sensitive for optical feedback. Furthermore, laser feedback can be eliminated to a high extent by ensuring that a reflected wave and an emitted laser pulse do not coincide inside the laser diode at the same time. Thus a constant laser output can be maintained (and misbehavior of a forward sense diode that may be incorporated inside the laser diode can be prevented) when the optical path length is changed slightly, e.g. due to heating of the cartridge and reader during magnetic actuation.

The laser modulator 22 can particularly switch the laser on and off at a high frequency, in the order of a few hundred MHz. It may be set in such a way that:

Laser light L1 is emitted in pulses $P_N$, at a high frequency (N=1, 2, 3, ... ).

The DC value of the current through the laser is set in such a way, that in between the pulses, the laser current is set well below the lasing threshold value, i.e. the laser is really 'off'.

When a light pulse $P_{N-1}$ is reflected from the carrier 11 back into the laser diode 21, the laser modulator 22 is set at such a frequency that the first relaxation oscillation of the reflected laser pulse $P_{N-1}'$ coincides with the first relaxation minimum of the currently emitted laser pulse $P_N$.

When the carrier density in the active layer of the laser device is a minimum then, the laser is less sensitive to optical feedback.

If the path length changes in the order of microns, this is not a problem since this shifts the reflected laser pulse only within a fraction of the relaxation period. In this way the problem is solved.

Figure 2:
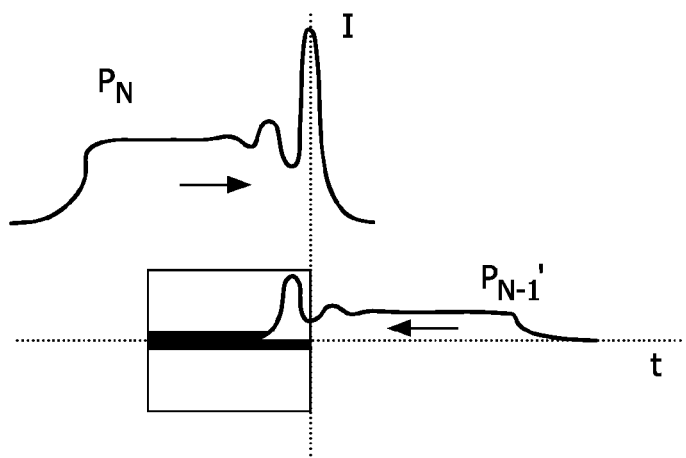
FIG. 2 illustrates the interference of an emitted laser pulse and a reflected previous laser pulse.

FIG. 2 illustrates the effect of the described laser modulation. The diagram shows (for a selected point inside the laser cavity) a currently generated pulse $P_N$ and an interfering reflected previous pulse $P_{N-1}'$ (vertical axis: intensity I; horizontal axis: time t). When the laser is operated in pulsed mode, the output of the laser shows fluctuations of the intensity I at the onset of the laser pulse due to the well known relaxation oscillations of laser diodes. If timing of the laser pulses is such that the first relaxation oscillation maximum of the externally reflected pulse $P_{N-1}'$ coincides with the first relaxation minimum in the currently emitted pulse $P_N$ (dashed line), the laser is rather insensitive to this optical feedback, due to a depletion of the carriers in the laser device at that time instance.

It should be noted that for external cavity lengths in the order of a few cm the cavity roundtrip time is less than 1 ns. If the laser pulse duration is in the order of 1 ns or more (typical for a few hundred MHz modulation frequency), the front end of a laser pulse $P_N$ is already reflected back at the laser, whereas the end of the same pulse is still being emitted. In this case an emitted laser pulse $P_N$ can only be influenced by its preceding pulse $P_{N-1}'$ after this preceding pulse has traveled back and forth several times in the external laser cavity. In this case, by tuning the modulation frequency, the first relaxation maximum of pulse $P_{N-1}'$ can be brought into overlap (in time domain) with the first relaxation minimum of pulse $P_N$. Unless very large external cavities are considered, an emitted laser pulse is always reflected back into the laser while it is still being emitted. Increased noise due to optical feedback can then only be achieved by modulating the laser current, thereby introducing spectral sidemodes and making the laser incoherent.

By choosing a high pulse level, an average high laser output level can still be reached. Furthermore, by choosing a rather low duty cycle (i.e. laser is only switched on during a very short period, after which a rather long "pause" is taken), a broad frequency range can be used, as the chance of a pulse entering the laser while it is switched 'on' is very low then. Furthermore, by exactly measuring the distance between the laser cavity and the window(s) of the carrier, an optimal value for the modulation frequency can be found. Thus the before mentioned "wiggle" of 1-2% could be reduced to $\frac{1}{1000}$ and less by using a 430 MHz modulation in experiments.

Figure 3:
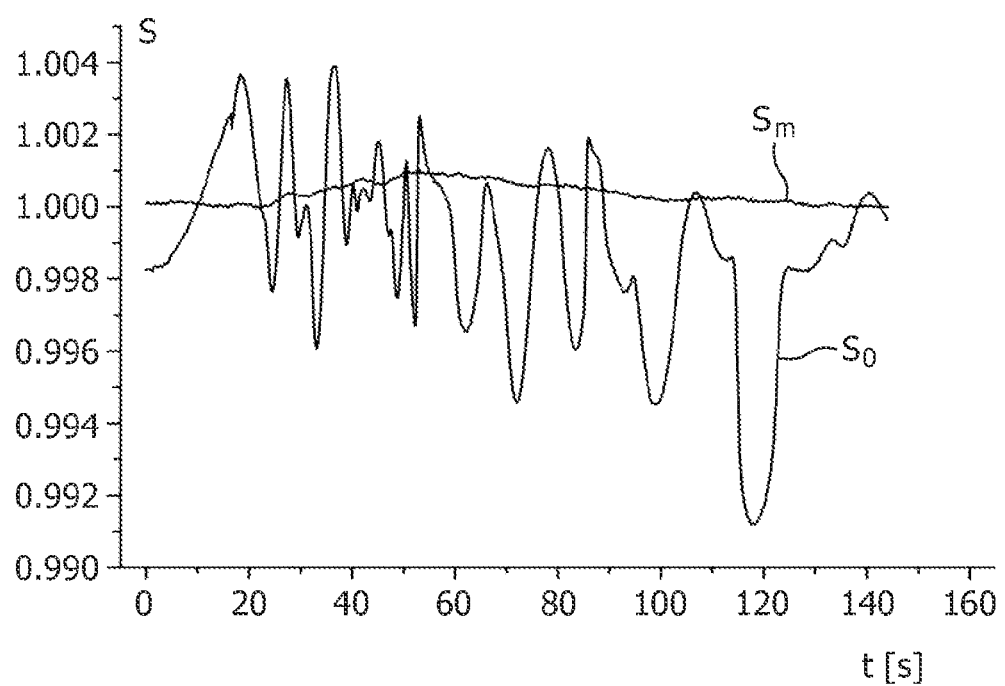
FIG. 3 illustrates a comparison between the laser output with and without a modulation according to the present invention.

FIG. 3 shows in a diagram the recorded normalized optical signal S (vertical axis) that is measured by the light detector 31 over time t (horizontal axis) when an empty cartridge is put in the microelectronic sensor device and when the actuation magnet 41 is switched on for 20 seconds. Ideally, the signal should not change, as there is no bioassay inside the cartridge. The diagram shows two curves:

1) curve $S_m$ with the laser modulator 22 switched on;
2) curve $S_0$ with the laser modulator 22 switched off.

From a comparison of these curves it is clear that the use of a modulator greatly enhances stability and adds extra robustness with respect to thermal expansion/shrinkage of the cartridge and/or reader during a measurement. The diagram also shows that the heating/cooling influences the measurement over a prolonged time, i.e. also after the magnets 41 have been switched off, due to expansion/shrinkage of the cartridge/reader.

It should be noted that at the detector side similar interference effects may occur. The output light beam L2 that hits the light detector 31 will partly be reflected from the detector back to the carrier 11. Some of this light will be transmitted back to the light source 21, and some light will be reflected back to the detector. This will cause some interference effects on both the detector as on the laser side. The use of a modulator 22 can prevent these things to occur (however, setting the light detector 31 at an angle with respect to the incoming output light beam L2 will also largely resolve these phenomena).

Furthermore, the use of a modulator 22 not only compensates for expansion/shrinkage of the cartridge. Also other influences that alter the optical path length can be compensated for, e.g. small movements or tiltings of the cartridge during a measurement.

While the invention was described above with reference to particular embodiments, various modifications and extensions are possible, for example:

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The particles serving as labels can be detected directly by the sensing method. As well, the particles can be further processed prior to detection. An example of further processing is that materials are added or that the (bio) chemical or physical properties of the label are modified to facilitate detection.

The device and method can be used with several biochemical assay types, e.g. binding/unbinding assay, sandwich assay, competition assay, displacement assay, enzymatic assay, etc. It is especially suitable for DNA detection because large scale multiplexing is easily possible and different oligos can be spotted via ink jet printing on the optical substrate.

The device and method are suited for sensor multiplexing (i.e. the parallel use of different sensors and sensor surfaces), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A microelectronic sensor device for optical examinations at a carrier, comprising:
   a light source for emitting an input light beam via an entrance window into the carrier; and
   a modulator for modulating the light source such that optical interferences of the light source with reflections of the input light beam from the entrance window or other components are reduced by modulation of the light source,
   wherein the light source comprises a laser, and wherein a laser current that drives the light source is modulated for introducing sidemodes in the input light beam for making the input light beam less coherent.

2. The microelectronic sensor device according to claim 1, wherein the modulation comprises a pulsed emission of the input light beam.

3. The microelectronic sensor device according to claim 2, wherein emitted pulses of the input light beam do not coincide in the light source with pulses reflected at the entrance window.

4. The microelectronic sensor device according to claim 2, wherein the light source comprises a laser, and wherein a relaxation minimum of a currently emitted pulse coincides in the light source with a relaxation maximum of a previous pulse reflected at the entrance window or at the other components of the carrier.

5. The microelectronic sensor device according to claim 2, wherein pulses of the input light beam have a repetition frequency that ranges between about 100 MHz and 1 GHz.

6. The microelectronic sensor device of claim 5, wherein the pulses of the input light beam have a duty cycle that ranges between about 1% and 80%.

7. The microelectronic sensor device according to claim 1, wherein the carrier comprises a contact surface at which the input light beam is totally internally reflected for exit from an exit window as an output light beam.

8. The microelectronic sensor device according to claim 7, wherein the output light beam is detected with a light detector.

9. The microelectronic sensor device according to claim 1, further comprising an actuator for manipulating target particles in a sample chamber adjacent to the carrier.

10. The microelectronic sensor device of claim 9, wherein the actuator comprises at least one electromagnet.

11. A method for optical examinations at a carrier, comprising the acts of:
    emitting from a light source an input light beam via an entrance window into the carrier; and
    modulating the light source with a laser modulator such that optical interferences of the light source with reflections of the input light beam from the entrance window or other components are reduced by modulation of the light source,
    wherein the light source comprises a laser, and wherein the modulating act modulates a laser current that drives the light source for introducing sidemodes in the input light beam for making the input light beam less coherent.

12. The method of claim 11, wherein the modulation comprises a pulsed emission of the input light beam, and wherein pulses of the input light beam have a repetition frequency that ranges between about 100 MHz and 1 GHz.

13. The method of claim 12, wherein the pulses of the input light beam have a duty cycle that ranges between about 1% and 80%.

14. The method of claim 11, wherein the carrier comprises a contact surface at which the input light beam is totally internally reflected for exit from an exit window as an output light beam, the method further comprising the act of detecting output light beam with a light detector.

15. The method of claim 11, further comprising the act of manipulating by an actuator target particles in a sample chamber adjacent to the carrier.

16. The method of claim 15, wherein the actuator comprises at least one electromagnet.

* * * * *